(12) United States Patent
Grunewald

(10) Patent No.: US 7,002,152 B2
(45) Date of Patent: Feb. 21, 2006

(54) SAMPLE PREPARATION FOR TRANSMISSION ELECTRON MICROSCOPY

(75) Inventor: Wolfgang Grunewald, Chemnitz (DE)

(73) Assignee: BAL-TEC AG, Balzers (LI)

( * ) Notice: Subject to any disclaimer, the term of this patent is extended or adjusted under 35 U.S.C. 154(b) by 364 days.

(21) Appl. No.: 10/410,828

(22) Filed: Apr. 10, 2003

(65) Prior Publication Data

US 2004/0164242 A1    Aug. 26, 2004

(30) Foreign Application Priority Data

Feb. 15, 2003  (CH) ..................................... 0225/03

(51) Int. Cl.
*G01N 1/28* (2006.01)
*G01N 1/04* (2006.01)

(52) U.S. Cl. ...................... 250/311; 250/306; 250/307; 250/492.1; 250/492.2; 250/492.21

(58) Field of Classification Search ................. 250/311, 250/306, 307, 492.1, 492.2, 492.21
See application file for complete search history.

(56) References Cited

U.S. PATENT DOCUMENTS

| | | | |
|---|---|---|---|
| 5,986,264 A * | 11/1999 | Grunewald | .................. 250/310 |
| 6,039,000 A * | 3/2000 | Libby et al. | .............. 118/723 E |
| 6,768,110 B1 * | 7/2004 | Alani | .......................... 250/307 |

* cited by examiner

*Primary Examiner*—Nikita Wells
(74) *Attorney, Agent, or Firm*—Notaro & Michalos PC

(57) ABSTRACT

TEM FIB samples of a solid state material are subsequently thinned through a subsequent treatment step free of contamination and free of destruction to extremely thin thicknesses through the alternate-sided bombardment of the sample surfaces with an ion beam, with which high-resolution observation and analysis of the sample material with a TEM becomes possible.

18 Claims, 2 Drawing Sheets

SAMPLE PREPARATION FOR TRANSMISSION ELECTRON MICROSCOPY

FIELD AND BACKGROUND OF THE INVENTION

The invention relates to a TEM FIB sample as well as to a method for the production of such a sample.

Samples for transmission electron microscopy (TEM) can be prepared in different ways. To be able to observe samples with a TEM, these must be thinned correspondingly defined such that they can be transmitted by electrons in the TEM. The quality of the image resolution is substantially dependent on the quality of the sample. For this purpose the sample must be uniformly set to a correspondingly desired defined thickness in a corresponding etching process. It is here important that in this etching process the sample structure is not altered by the process itself. However, this does not yield the desired quality of the sample appropriate to current requirements. The wet-chemical etching method does not lead to the desired goal.

For this reason, for high-quality TEM samples the samples are today worked by etching with a fixed argon ion beam having, for example, a diameter of approximately 1 mm. A further known method, and one preferred today, comprises cutting out the sample with a focused ion beam (FIB technique) and to thin it as desired. Herein a finely focused scanning gallium ion beam with a beam diameter of a few nm is employed, with the aid of which TEM samples can be prepared from the solid material in the form of lamellae by perpendicular bombardment of the surface. Typically the sample lamellae are herein approximately 80 to 100 nm thick. This latest FIB preparation technique is described for example in P. Gnauck, P. Hoffrogge, ICEM 15, Durban, (Suppl. 1: Proceedings), (2002) 3, 32.

The technique for producing FIB samples for TEM lamellae does, however, have various disadvantages. The lamella cannot be prepared of sufficient thinness for the samples to be well suited for high-resolution transmission electron microscopy (HRTEM). The TEM lamella is moreover contaminated through the preparation and, in comparison to conventional ion beam preparation with fixed ion beam, has significantly greater margin amorphization. This margin amorphization is a disturbance of the original structure in the surface of the sample and specifically on both sides of the sample and this occurs to a depth of approximately 20 nm on both sides of the sample. In conventional sample production by means of fixed ion beam etching, this destruction of the original structure extends only to a depth of approximately 5 nm. However, the advantages, such as for example the target precision of the scanning FIB technique cannot be attained.

The above listed problems lead to a strongly reduced sample quality. To be able to solve these problems, attempts have recently been made to subsequently thin the FIB samples with the aid of conventional non-scanning ion beam preparation. But, due to the sample geometry and the etching on one side of the lamella, additional undesirable contamination occurs. Such contaminations negate the advantage of the subsequent treatment and make the sample unusable. The problematic issue in subsequent working of FIB samples is described in prior art in Max V. Siderov, Microsc. Microanal. 8 (Suppl. 2: Proceedings), (2002) 560 CD.

The invention addresses the problem of eliminating the disadvantages of prior art, but in particular of realizing TEM samples, which make possible a high quality, but in particular a high resolution and detail reproduction when observing with the TEM.

SUMMARY OF THE INVENTION

The problem is solved according to the invention through the device claimed and through the approach following the method claimed. Further advantageous embodiments and method steps are also claimed.

The formation according to the invention of a sample, in particular of a sample lamella, permits the production of a sufficiently thin lamella, which during the TEM observation can resolve and image a high degree of detail of the original sample material. For this purpose according to the invention a coarse sample produced with the FIB technique is subsequently worked with an ion beam and thinned or etched to the requisite thickness. The subsequent working of the sample must be free of contamination, which means no foreign material, such as ambient material or none of the original material must again be deposited onto the sample during the etching process. A further important aspect comprises that in this subsequent working the material structure of the sample is not altered on the surface, or that the original structure of the sample material is retained. Since the FIB sample as the starting sample already has structural disturbances, such as margin amorphization, on the surfaces, which are inherent to the FIB technique, and extend approximately to a depth of 20 nm into each sample side, it is necessary that the subsequent working technique can to a substantial extent eliminate such areas of disturbance in order to expose the original not affected material which is to be analyzed. According to the invention this is attained thereby that the sample is bombarded and ablated alternately on both sides by an ion beam at a bombardment angle. It becomes thereby possible to avoid to a large extent contaminations, which is absolutely necessary for high-resolution transmission electron microscopy (HRTEM). The method according to the invention now also permits producing the appropriately thin samples of less than 40 nm thickness, even preferably of less than 20 nm thickness, which are required for this high-resolution technology. A further advantage comprises that the subsequent working according to the invention is applicable to all FIB sample types and does not depend on the sample geometry. Complicated sample geometries can thus also be worked subsequently.

In order to avoid preferential directions of the ion beam etching, thus undesired scoring structures on the sample surface, it is advantageous to move, in addition, the sample relative to the ion beam. Such movements can be oscillating movements and be carried out as periodic tilting movements of the sample relative to the direction of incidence of the ion beam. This movement should be relatively slow and uniform. The tilting can advantageously take place by an angle of up to ±70 degrees relative to the ion beam direction and the movement frequency approximately in a range of 0.1 Hz.

The various features of novelty which characterize the invention are pointed out with particularity in the claims annexed to and forming a part of this disclosure and are entirely based on the Swiss priority application number 2003 0225/03 filed Feb. 15, 2003. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the following the invention will be explained in further detail by example and in conjunction with schematic drawings wherein.

DESCRIPTION OF THE PREFERRED EMBODIMENTS

Figure 1:
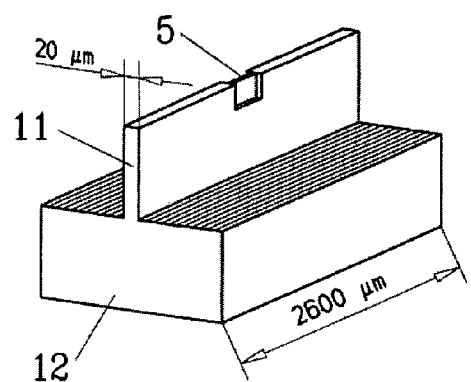
FIG. 1 illustrates a mechanical preparation step for the production of an FIB sample according to prior art.

For the production of an FIB sample from the solid body material, for example from a semiconductor wafer, a sample piece 12 is removed and on it through mechanical sawing a web 11 is roughed out, such as is shown for example in FIG. 1. The sample piece 12 is approximately 2600 µm long and the width of the web is approximately 20 µm. On the front face of the web 11 in a partial region where the lamella sample 5 is to be generated, a protective coating is applied which serves as masking for the subjacent lamella 5 which is to be etched out. With a focused ion beam (FIB) impinging perpendicularly on the front face of the web the lamella 5 is now exposed by depth etching. This is schematically shown in FIG. 2 by the arrow with the label "FIB etching".

Figure 2:
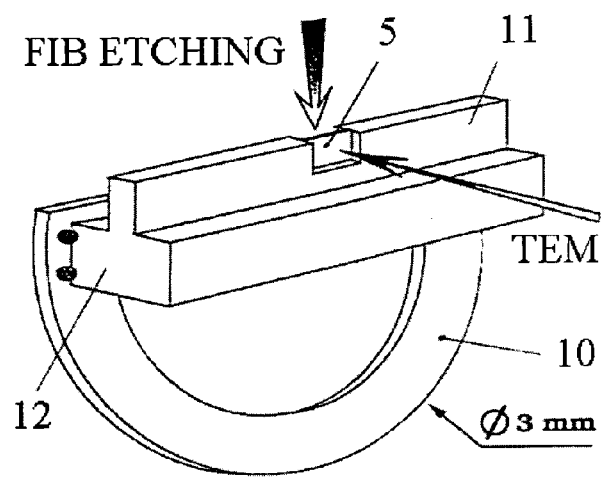
FIG. 2 illustrates a mounting and the FIB working of the preparation according to FIG. 1 within the prior art.

The sample piece 12 with the lamella sample 5 is now disposed on a sample holder 10 with a diameter of for example 3 mm, and can now be observed in the TEM, as is also indicated schematically in FIG. 2 by the arrow and the associated label "TEM".

Figure 3:
FIG. 3 a three-dimensional representation of a completed FIB sample in a scanning electron microscope image according to prior art.
Figure 4:
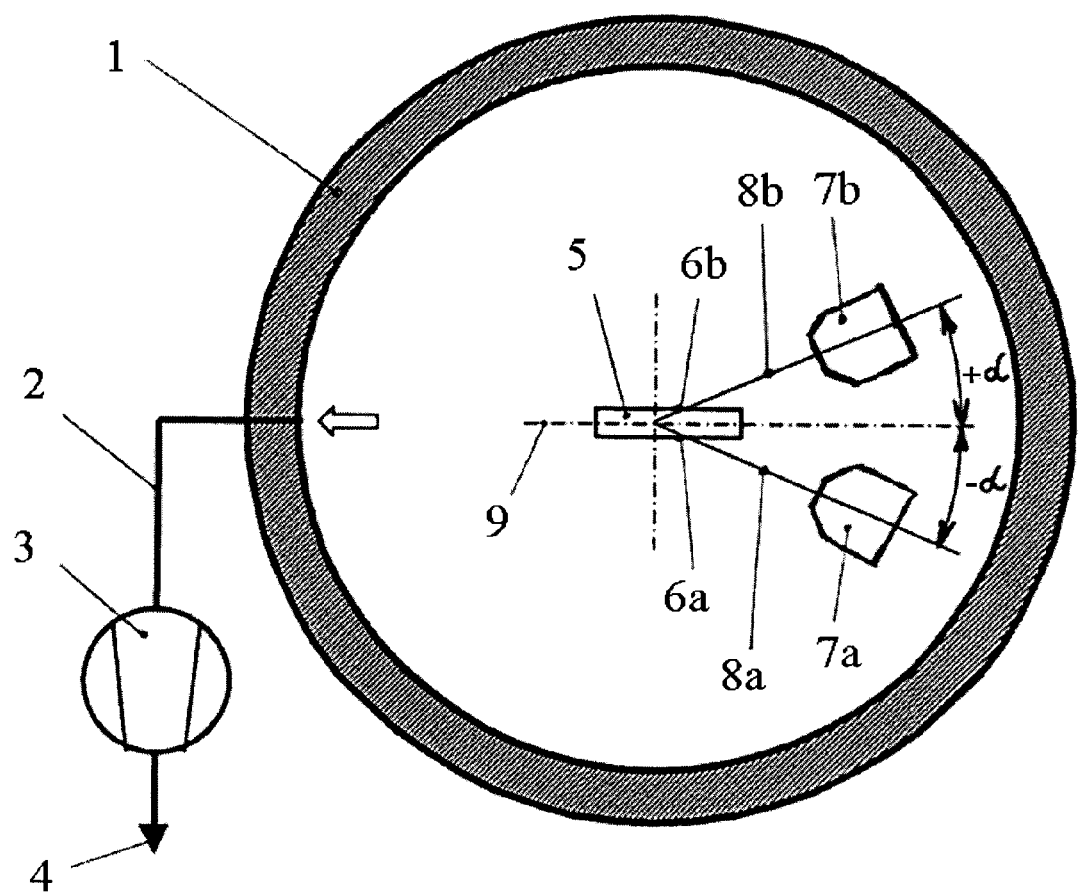
FIG. 4 a configuration for the subsequent treatment according to the invention of an FIB sample.

In FIG. 3 a scanning electron microscopic (REM) image reproduction of such a sample 5 is shown for better illustration. It is therein also evident that the FIB-etched lamella of such sample (FIB etching) is relatively thick. In the lower region of the sample can be seen a high waviness of the material which also shows that in the etching, respectively sputtering process, contaminations occur through the redeposition of the involved surfaces 6a, b. The scanning FIB ion beam must be operated with energies between 5 keV to 30 keV, due to the necessary focusing. This leads to the corresponding damage or disturbances of the material structure on both sides of the lamella surfaces 6a and 6b of sample 5, typically to a depth of approximately 20 nm.

According to the invention now an FIB sample, which already has a corresponding lamella structure 5, is placed in a vacuum chamber 1 in its sample disposition axis or plane 9, in order to be subsequently treated appropriately. The chamber 1 is evacuated in known manner via a pump-down line 2 with a vacuum pump 3, for example a turbo vacuum pump, with pump outlet 4. In the vacuum chamber 1 is, moreover, disposed an ion source 7, which can be directed obliquely at an angle α relative to the sample disposition plane 9 with its ion beam 8 onto the sample surfaces 6a and 6b. The sample 5 can be etched with the ion source 7 through the ion bombardment on both sides on their surfaces 6a and 6b and consequently be thinned to the desired dimension. According to the invention the ion beam 8 should be directed alternately 8a, b onto the one side 6a as well as also onto the other side 6b of sample 5. Through this alternating of both sample sides 6a, b a redeposition and thus a contamination of the surfaces 6a, b can be avoided. The alternating etching of surfaces 6a and 6b advantageously takes place through a periodic changing of the sides of sample 5. This can take place through a back and forth movement 7a, b of the ion source 7 about the sample disposition axis 9, as well as also by corresponding tilting movements of sample 5 itself with the ion source 7 being stationary. Critical is herein the alternating etching of sample surfaces 6a and 6b, which can be achieved with a relative movement between the direction of the ion beam 8 and the surfaces 6a and 6b of sample 5. The ion beam 8 with its positions 8a and 8b should herein impinge obliquely onto the sample surfaces 6a and 6b according to the depicted bombardment angle +α and −α relative to the sample disposition plane 9. The alternating treatment of the sample surfaces 6a and 6b are advantageously carried out through pendulum-like relative movements about the angular range +α/−α. The ion beam herein travels also through the zero-degree angle, which coincides with the sample disposition plane 9. Contaminations of sample 5 are hereby effectively avoided. To attain good results, according to the invention a bombardment angular range +/−α must be traversed which traverses the values in the range of +/−4° to +/−45°. Especially good results are attained for the angular bombardment range +/−α in the value range of +/−4° to +/−20°.

In the alternating working it must be ensured that each side of the sample is worked at least twice with the ion beam. However, it is especially advantageous if each side of the sample is worked several times. The length of time of the beam action per working step depends on the original thickness and the quantity of the material to be taken off. In the known FIB samples and with the desired results, work advantageously takes place in a range of a few seconds up to a few minutes per side and step.

Of the disturbed structure region of the FIB sample surface 6a, b according to the invention as much as possible is to be ablated. The maximum remaining disturbance depth of the two surfaces 6a, b should be maximally 10 nm after the working, and, according to the approach according to the invention, preferably maximally 5 nm disturbed material is to remain on the surfaces 6a, b.

Such high-resolution samples for HRTEM application, which are less than 40 nm thick or preferably even less than 20 nm, are especially suited for sample materials in the field of semiconductor inspections, in particular for semiconductors which comprise materials such as Si, GaAs or Ge.

The subsequent treatment can according to the invention also be especially well automated by employing corresponding programmable controls. The time cycle, the number of etching steps and the bombardment angle, as well as also the movement course can be preset or programmed as desired and can be completed automatically. The entire preparation process can consequently be appropriately automated with the aid of a preparation program and can be adapted individually to the samples 5 to be generated. The automatic subsequent treatment of samples 5 consequently does not demand the continuous presence of the operator and thereby becomes time-saving, reproducible and can be realized economically.

For further clarification the subsequent working according to the invention of an FIB sample will be described in conjunction with an example. As the starting material is used an FIB section or lamella 5 comprised of silicon material with a protective platinum layer 13. The lamella is 6 µm deep, including the protective platinum layer 13, and 13 µm wide. For the subsequent thinning according to the invention an ion thinning was applied in an installation RES 100 by Baltec AG, FL-9496 Balzers, Liechtenstein, which is especially suited for this application. An etching program was employed, which permits the automatic change of the direction of bombardment of the ion source. The sample holder was changed in each instance after one minute from position +α=15° to position −α=−15°. The acceleration voltage of the ion source 7 was 2 keV and the ion current 1.3 mA. In addition to the changing angle of bombardment +/−α from maximally +/−15°, with respect to the lamella surface, the sample was oscillated by +/−20°, thus tilted back and forth relative to the direction of incidence of the ion beam at a cycle of approximately 0.1 Hz to avoid a preferential direction of the etching beam on the sample. The model sample was first etched for a total of eight minutes, subsequently inspected and then additionally etched for ten minutes, subsequently inspected and then additionally etched for ten minutes and also inspected and lastly again additionally etched for three minutes; the sample was consequently etched for a total of 21 minutes. As a result, samples could be obtained which, after the first step, were already thinner than 40 nm and after the additional steps were already in the range of 20 nm and below without significant contamination of the surfaces. As a consequence, according to the inventive approach, high-resolution TEM images that were faithful as to detail could be obtained.

While specific embodiments of the invention has been shown and described in detail to illustrate the application of the principles of the invention, it will be understood that the invention may be embodied otherwise without departing from such principles.

What is claimed is:

1. TEM FIB sample of a solid state material having an undisturbed original material structure, which sample is adjusted with a subsequent treatment step on its opposite surfaces by alternating bombardment of the opposite surfaces at alternating acute angles with a single moving ion beam to a desired thickness, wherein the thickness is <40 nm, and wherein the sample consists mainly of the undisturbed original material structure.

2. Sample as claimed in claim 1, wherein the thickness is <20 nm.

3. Sample as claimed in claim 1, wherein the sample (5) on its surfaces (6a, b) has substantially no contamination.

4. Sample as claimed in claim 1, wherein the fraction of the disturbed structure on both sides of the sample surfaces (6a, b) has a disturbance depth of maximally 10 nm.

5. Sample as claimed in claim 1, wherein the fraction of the disturbed structure on both sides of the sample surfaces (6a, b) has a disturbance depth of maximally 5 nm.

6. Sample as claimed in claim 1, wherein the sample (5) is comprised of semiconductor material.

7. A method for production of a TEM FIB sample of a solid state material, comprising: subsequently etching the sample (5) through a subsequent working step on both sides to a desired thickness with a single ion beam (8) being guided at a bombardment angle (α) relatively, alternatively on the one side (6a) and on the other side (6b) of the sample (5) and wherein the bombardment angle (α) is set to values in the range +/−4° to +/−20°.

8. A method as claimed in claim 7, wherein the sample (5) and/or the ion beam (8) is moved relatively in the manner of a pendulum with respect to the sample (5) with reference to the sample disposition plane (9) about the angle +/−α.

9. A method as claimed in claim 8, wherein the pendulum movement takes place with continuous movement.

10. A method as claimed in claim 7, wherein the structurally disturbed surface region (6a, b) of the FIB sample (5) is ablated such that the remaining sample (5) is comprised mainly of the original undisturbed material.

11. A method as claimed in claim 10, wherein the remaining residual disturbance depth is maximally 10 nm.

12. A method as claimed in claim 11, wherein the subsequently treated sample (5) has a thickness of <40 nm.

13. A method as claimed in claim 11, wherein the subsequently treated sample (5) has a thickness of <20 nm.

14. A method as claimed in claim 10, wherein the remaining residual disturbance depth is maximally 5 nm.

15. A method as claimed in claim 7, wherein the subsequent treatment takes place such that the sample surface (6a, b) has substantially no contamination.

16. A method as claimed in claim 7, wherein the ion beam (8) is operated with an energy of 200 eV to 10 keV and preferential scanning does not take place over the sample (5).

17. A method as claimed in claim 7, wherein the sample (5) is a semiconductor material.

18. A method as claimed in claim 7, wherein the alternate-sided subsequent treatment of the sample (5) is automated with a process control.

\* \* \* \* \*